US009981090B2

(12) United States Patent
Hogan

(10) Patent No.: US 9,981,090 B2
(45) Date of Patent: May 29, 2018

(54) METHOD FOR PRODUCING AN APERTURE PLATE

(71) Applicant: Stamford Devices Limited, Dangan, Galway (IE)

(72) Inventor: Brendan Hogan, Gort (IE)

(73) Assignee: STAMFORD DEVICES LIMITED, Galway (IE)

( * ) Notice: Subject to any disclaimer, the term of this patent is extended or adjusted under 35 U.S.C. 154(b) by 441 days.

(21) Appl. No.: 13/902,096

(22) Filed: May 24, 2013

(65) Prior Publication Data

US 2013/0334338 A1 Dec. 19, 2013

Related U.S. Application Data

(60) Provisional application No. 61/658,054, filed on Jun. 11, 2012.

(51) Int. Cl.
| | |
|---|---|
| *C25D 1/08* | (2006.01) |
| *A61M 11/00* | (2006.01) |
| *C25D 7/00* | (2006.01) |
| *B05B 17/00* | (2006.01) |
| *C25D 3/56* | (2006.01) |

(52) U.S. Cl.

CPC ......... *A61M 11/003* (2014.02); *A61M 11/005* (2013.01); *C25D 1/08* (2013.01); *C25D 7/00* (2013.01); *B05B 17/0646* (2013.01); *C25D 3/567* (2013.01)

(58) Field of Classification Search
CPC .......... C25D 1/08; C25D 7/00; A61M 11/003; A61M 11/005
See application file for complete search history.

(56) References Cited

U.S. PATENT DOCUMENTS 3,130,487 A * 4/1964 Mears .................... C25D 1/08 29/424

3,325,319 A * 6/1967 Frantzen .................. C23F 1/02 216/41

(Continued)

FOREIGN PATENT DOCUMENTS

CN 1149907 A 5/1997

DE 1948135 A1 4/1971

(Continued)

OTHER PUBLICATIONS

International Search Report and Written Opinion for corresponding International Application No. PCT/EP2013/060803, dated Jun. 11, 2014, 11 pages.

(Continued)

*Primary Examiner* — Stefanie S Wittenberg
(74) *Attorney, Agent, or Firm* — Bookoff McAndrews, PLLC

(57) ABSTRACT

A photo-resist is applied in a pattern of vertical columns having the dimensions of holes or pores of the aperture plate to be produced. This mask pattern provides the apertures which define the aerosol particle size, having up to 2500 holes per square mm. There is electro-deposition of metal into the spaces around the columns. There is further application of a second photo-resist mask of much larger (wider and taller) columns, encompassing the area of a number of first columns. The hole diameter in the second plating layer is chosen according to a desired flow rate.

24 Claims, 6 Drawing Sheets

(56) References Cited

U.S. PATENT DOCUMENTS

| | | | |
|---|---|---|---|
| 4,184,925 A | 1/1980 | Kenworthy | |
| 4,379,737 A | 4/1983 | Mearig | |
| 4,430,784 A * | 2/1984 | Brooks | B41J 2/162 205/150 |
| 4,628,165 A | 12/1986 | Nobel et al. | |
| 4,839,001 A | 6/1989 | Bakewell | |
| 4,844,778 A | 7/1989 | Witte | |
| 4,849,303 A * | 7/1989 | Graham | C25D 3/56 200/266 |
| 4,972,204 A | 11/1990 | Sexton | |
| 5,164,740 A | 11/1992 | Ivri | |
| 5,373,629 A | 12/1994 | Hupe et al. | |
| 5,443,713 A | 8/1995 | Hindman | |
| 5,560,837 A * | 10/1996 | Trueba | B41J 2/162 205/127 |
| 5,565,113 A | 10/1996 | Hadimioglu et al. | |
| 5,586,550 A | 12/1996 | Ivri et al. | |
| 5,646,662 A | 7/1997 | Kitahara | |
| 5,685,491 A | 11/1997 | Marks et al. | |
| 5,758,637 A | 6/1998 | Ivri et al. | |
| 5,766,441 A | 6/1998 | Arndt et al. | |
| 5,899,390 A | 5/1999 | Arndt et al. | |
| 5,921,474 A * | 7/1999 | Zimmermann | F02M 61/168 239/585.1 |
| 5,976,342 A * | 11/1999 | Arndt | B05B 1/34 205/122 |
| 6,050,507 A * | 4/2000 | Holzgrefe | F02M 51/0671 239/585.1 |
| 6,074,543 A * | 6/2000 | Yoshihira | B41J 2/14024 205/75 |
| 6,205,999 B1 | 3/2001 | Ivri et al. | |
| 6,235,177 B1 | 5/2001 | Borland et al. | |
| 6,310,641 B1 | 10/2001 | Mrvos et al. | |
| 6,357,677 B1 | 3/2002 | Ren et al. | |
| 6,586,112 B1 | 7/2003 | Te | |
| 6,605,866 B1 * | 8/2003 | Crowley | H01L 23/3107 257/692 |
| 6,773,094 B2 | 8/2004 | Linliu et al. | |
| 7,066,398 B2 | 6/2006 | Borland et al. | |
| 7,104,475 B2 | 9/2006 | Goenka et al. | |
| 7,259,640 B2 * | 8/2007 | Brown | G01P 15/0802 333/160 |
| 8,398,001 B2 | 3/2013 | Borland et al. | |
| 2001/0013554 A1 | 8/2001 | Borland et al. | |
| 2002/0063751 A1 | 5/2002 | Aizawa et al. | |
| 2002/0157956 A1 * | 10/2002 | Ikeda | B41J 2/1433 205/75 |
| 2003/0231227 A1 | 12/2003 | Kim | |
| 2004/0035413 A1 * | 2/2004 | Smaldone | A61M 15/00 128/200.23 |
| 2006/0055739 A1 | 3/2006 | Kim et al. | |
| 2006/0086689 A1 | 4/2006 | Raju | |
| 2006/0203036 A1 | 9/2006 | Sexton et al. | |
| 2007/0023547 A1 | 2/2007 | Borland et al. | |
| 2007/0212653 A1 | 9/2007 | Hori | |
| 2010/0055045 A1 * | 3/2010 | Gerhart | A61K 9/0078 424/45 |
| 2010/0282247 A1 * | 11/2010 | Kadrichu | A61K 9/0078 128/200.14 |
| 2013/0252020 A1 | 9/2013 | Hradil | |
| 2013/0334339 A1 | 12/2013 | Xu | |
| 2015/0101596 A1 | 4/2015 | Hogan | |
| 2015/0336115 A1 | 11/2015 | Hogan et al. | |
| 2016/0130715 A1 | 5/2016 | Xu | |

FOREIGN PATENT DOCUMENTS

| | | | |
|---|---|---|---|
| DE | 2050285 A1 | 5/1972 | |
| DE | 19527846 | 1/1997 | |
| EP | 1199382 A1 | 4/2002 | |
| EP | 1810743 | 7/2007 | |
| EP | 2204238 A1 | 7/2010 | |
| GB | 2240494 A | 8/1991 | |
| JP | 4-183892 | 6/1992 | |
| JP | H04-322290 | 11/1992 | |
| JP | H05-239682 | 9/1993 | |
| JP | H05-74669 | 10/1993 | |
| JP | 7-329304 | 12/1995 | |
| JP | 10-507243 | 7/1998 | |
| JP | 10-228114 * | 8/1998 | G03F 7/12 |
| JP | 11138827 A | 5/1999 | |
| JP | 2002019125 | 1/2002 | |
| JP | 2002-166541 | 6/2002 | |
| JP | 2002187374 A | 7/2002 | |
| JP | 2002-289097 | 10/2002 | |
| JP | 2006-056151 * | 3/2006 | B41F 15/44 |
| JP | 20060297688 | 11/2006 | |
| JP | 2008-545525 | 12/2008 | |
| RU | 2078405 | 4/1997 | |
| WO | WO 91/03920 A2 | 3/1991 | |
| WO | WO 01/18280 | 3/2001 | |
| WO | WO 01/071065 | 3/2001 | |
| WO | WO 2006/127181 | 11/2006 | |
| WO | WO-2009042187 A1 | 4/2009 | |
| WO | WO 2011/083380 A1 | 7/2011 | |
| WO | WO-2011139233 A1 | 11/2011 | |
| WO | WO 2012/092163 A | 7/2012 | |
| WO | WO 2013/186031 A | 12/2013 | |

OTHER PUBLICATIONS

Lu et al., Grain Refinement in the Solidification of Undercooled Ni-Pd Alloys, Journal of Crystal Growth, 309:103-111 (2007).

Vecellio, L. "The mesh nebuliser: a recent technical innovation for aerosol delivery," Breathe, vol. 2, No. 3, Mar. 2006 (10 pages).

* cited by examiner

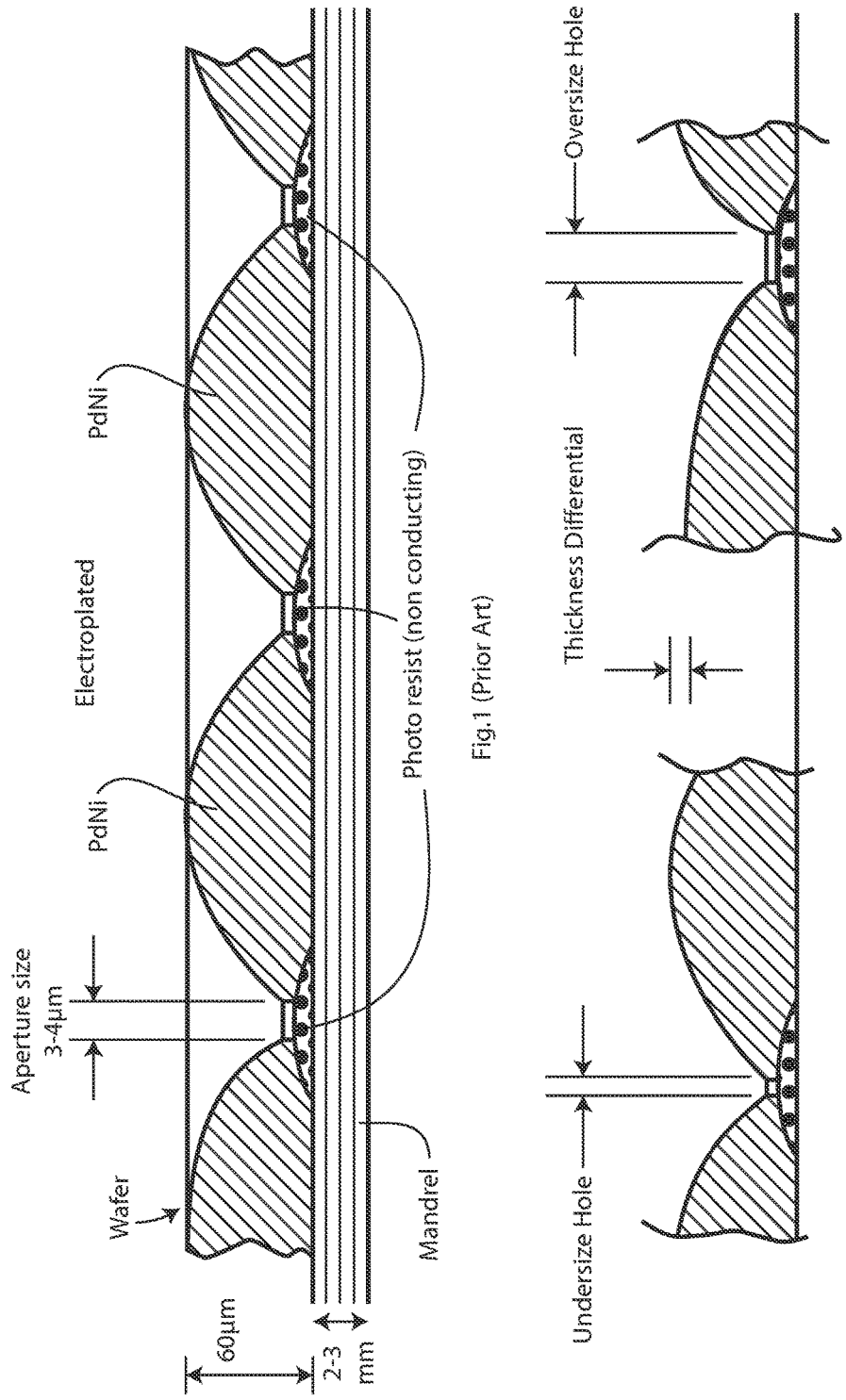

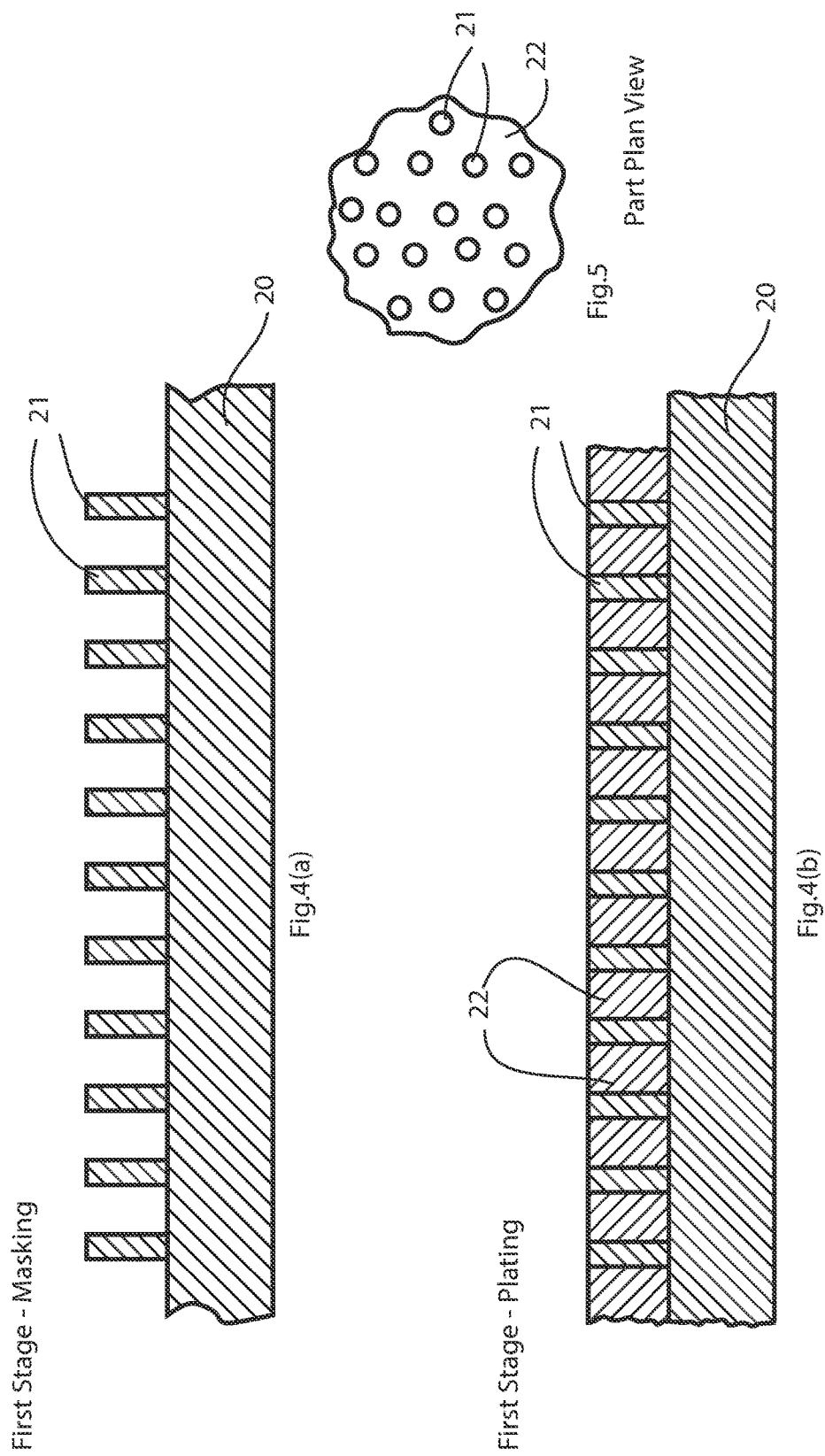

Second Stage - Masking

Second Stage - Plating

Thickness of second layer — Fig.8
Thickness of first layer

Fig.8

Aerosol

Domed to form vibrating plate

Prior Art

Invention

Particle Size

Small particle size possible

Higher Flow Rates Possible 0     0.5    1 ml/min 1.4ml/min

Flow Rate

Fig.10

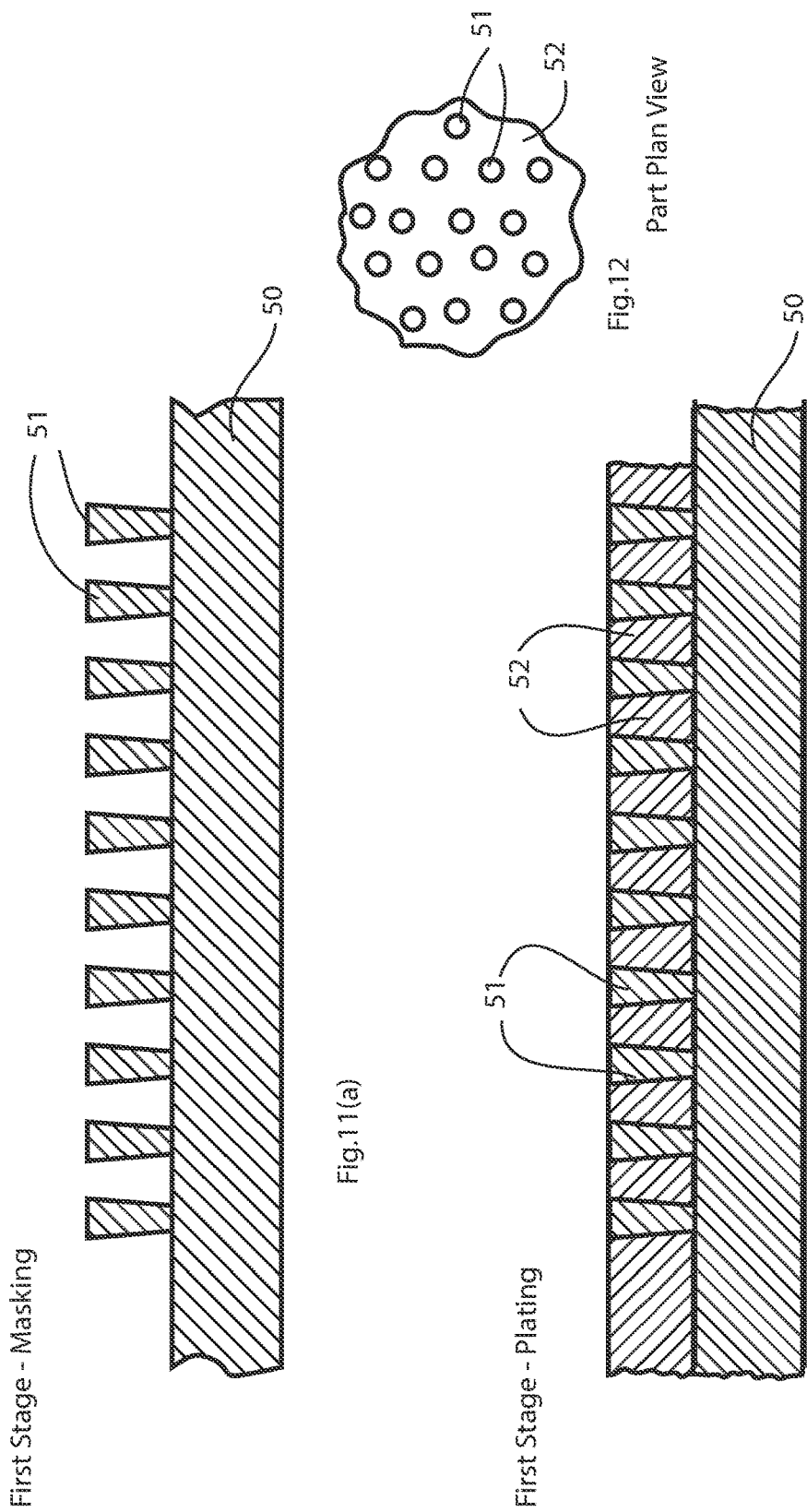

METHOD FOR PRODUCING AN APERTURE PLATE

CROSS-REFERENCE TO RELATED APPLICATIONS

This application claims the benefit of U.S. Provisional Patent Application Ser. No. 61/658,054, filed on Jun. 11, 2012, which is incorporated herein by reference in its entirety.

INTRODUCTION

The invention relates to manufacture of aperture plates (or "vibrating membranes") for aerosol (or "nebulizer") devices.

An aperture plate is used for aerosol delivery of liquid formulations delivering a controlled liquid droplet size suitable for pulmonary drug delivery. The ideal nebulizer is one which assures a consistent and accurate particle size in combination with an output rate that can be varied to deliver the drug to the targeted area as efficiently as possible. Delivery of the aerosol to the deep lung such as the bronchi and bronchiole regions requires a small and repeatable particle size typically in the range of 2-4 μm. In general, outputs greater than 1 ml/min are required.

Currently, aperture plates are produced by a variety of different means, including electroplating and laser drilling. Electroplating is generally the most advantageous production method from a technical and economic standpoint. U.S. Pat. No. 6,235,177 describes an approach based on electroplating, in which a wafer material is built onto a mandrel by a process of electro-deposition where the liquefied metals in the plating bath (typically Palladium and Nickel) are transferred from the liquid form to the solid form on the wafer. Material is transferred to the conducting surface on the mandrel and not to the photo resist areas which are non-conducting. Areas are masked with non-conductive photo resist where metallic build-up is not required, see FIG. 1. After the conclusion of the plating process, the mandrel/wafer assembly is removed from the bath and the wafer peeled from the mandrel for subsequent processing into an aperture plate.

However, a problem with this approach is that the hole size is dependent on the plating time and the thickness of the resulting wafer. The process can be difficult to control, and if not perfectly controlled some holes may be near closed or blocked as shown in FIG. 2, or over-sized as shown in FIG. 3, and there may be out-of-tolerance variation in the sizes of the holes Also, there are limitations on the number of holes per unit of area. Further, with this technology an increase in output rate usually requires an increase in particle size, which generally may not be desired. It is more desired to increase output rate without increasing particle size.

Combinations of hole size accuracy and number of holes per unit of area can be a significant determinant in the nebulizer output rate and resulting particle size distribution.

WO 2011/139233 (Agency for Science, Technology and Research) describes a microsieve manufactured using SU8 material with photo-masking.

U.S. Pat. No. 4,844,778 (Stork Veco) describes manufacture of a membrane for separating media, and a separation device incorporating such a membrane. The manufacturing method includes a two step photolithographic procedure.

EP1199382 (Citizen watch Co. Ltd.) describes a production method for a hole structure in which there is exposure to photosensitive material in multiple cycles to provide deeper holes tapered towards the top because there is exposure through the first holes.

The invention is directed towards providing an improved method for manufacture of an aperture plate to address the above problems.

SUMMARY OF THE INVENTION

According to the invention, there is provided a method of manufacturing an aperture plate wafer, the method comprising providing a mandrel of conductive material, applying a mask over the mandrel in a pattern of columns, electroplating the spaces around the columns, removing the mask to provide a wafer of the electroplated material with aerosol-forming holes where the mask columns were.

In one embodiment, the columns have a depth in the range of 5 μm to 40 μm, and preferably 15 μm to 25 μm.

In one embodiment, the columns have a width dimension in the plane of the mandrel in the range of 1 μm to 10 μm, preferably 2 μm to 6 μm.

In one embodiment, the electroplating is continued until the plated material is substantially flush with the tops of the columns.

In one embodiment, there is substantially no overlap between the plated material and the mask material.

Preferably, said masking and plating steps are followed by at least one subsequent second cycle of masking and plating to increase the wafer thickness.

In one embodiment, the subsequent plating step or steps bring the overall wafer thickness up to above 50 μm, and preferably greater than 58 μm.

In one embodiment, the subsequent plating step or steps bring the overall wafer thickness up to a level desired according to criteria for removal of the wafer from the mandrel, and/or desired frequency of operation of the aperture plate, and/or physical constraints of a nebulizer drive.

In one embodiment, the spaces revealed by removal of the subsequent mask each overlay a plurality of aerosol-forming holes, and the subsequent plating occludes some of the holes formed by the first plating step.

In one embodiment, the extent of occlusion is chosen according to desired flow rate through the end product aperture plate.

In one embodiment, the first masking and plating are performed so that the aerosol-forming holes are tapered in a funnel-shape.

In one embodiment, the subsequent masking and plating are performed so that the overlay spaces are tapered in a funnel shape.

In one embodiment, the plated metal includes Ni. In one embodiment, the plated metal includes Pd. In one embodiment, both Ni and Pd are present. Preferably, the proportion of Pd is in the range of 85% w/w and 93% w/w, and preferably about 89%, substantially the balance being Ni.

In one embodiment, the method comprise the further steps of further processing the wafer to provide an aperture plate ready to fit into an aerosol-forming device. In one embodiment, the wafer is punched into a non-planar shaped aperture plate. In one embodiment, the wafer is punched into a shape having an operative dome-shaped part and a flange for engaging a drive. Preferably, the wafer is annealed before punching.

In another aspect, the invention provides an aperture plate wafer comprising a body of metal whenever formed in a method as defined above in any embodiment.

In another aspect, the invention provides an aperture plate whenever manufactured by a method as defined above in any embodiment.

In another aspect, the invention provides an aerosol-forming device comprising an aperture plate as defined above, and a drive engaging the plate to vibrate it at a desired frequency for forming an aerosol.

In another aspect, the invention provides an aperture plate wafer comprising a bottom layer of plated metal with aerosol-forming through holes and at least one top layer of metal having large holes, in which said large holes overlie a plurality of aerosol-forming holes.

In one embodiment, the top layer occludes some of the holes in the bottom layer.

In one embodiment, the number of aerosol-forming holes per large hole is related to a desired aerosol flow rate.

In one embodiment, the metal of all layers is the same.

In another aspect, the invention provides an aperture plate including a wafer as defined above in any embodiment.

In another aspect, the invention provides an aerosol-forming device comprising an aperture plate as defined above, and a drive engaging the plate to vibrate it at a desired frequency for forming an aerosol.

DETAILED DESCRIPTION OF THE INVENTION

The invention will be more clearly understood from the following description of some embodiments thereof, given by way of example only with reference to the accompanying drawings in which:

FIGS. 1 to 3 are cross-sectional diagrams outlining a prior art process as described above;

FIGS. 4(a) and 4(b) are cross-sectional views showing masking and plating steps for a first stage of the method, and FIG. 5 is a part plan view of the wafer for this stage;

FIGS. 6(a) and 6(b) are cross-sectional views showing a second masking and plating stage, and FIG. 7 is a plan view;

FIG. 8 is a cross-sectional view after resist removal;

FIG. 9 shows the wafer after punching to form the final aperture plate shape;

FIG. 10 is a plot of particle size vs. flow rate to illustrate operation of the aperture plate;

Figure 6A:
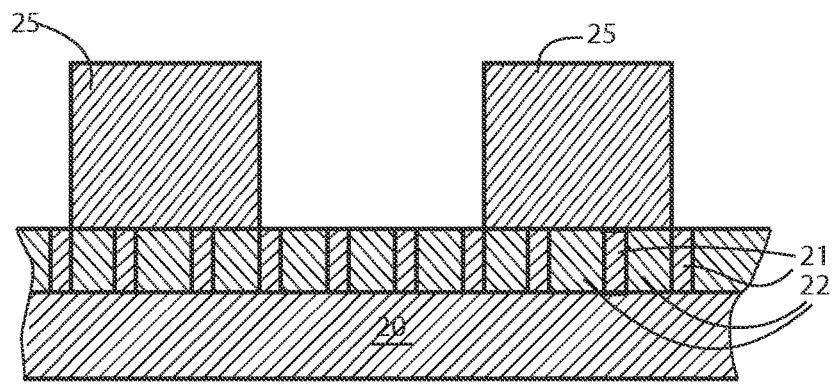
Figure 6B:
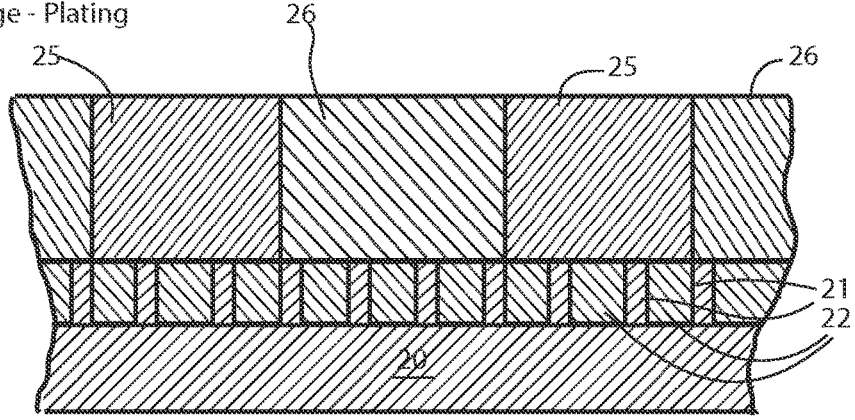
Figure 7:
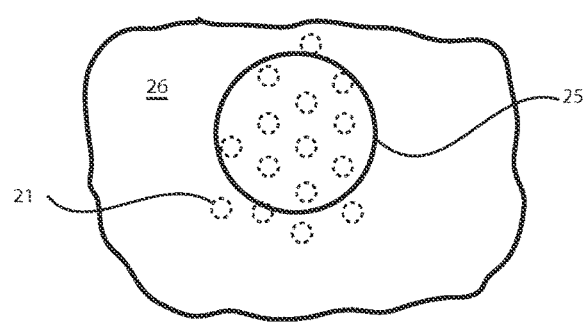
Figure 13A:
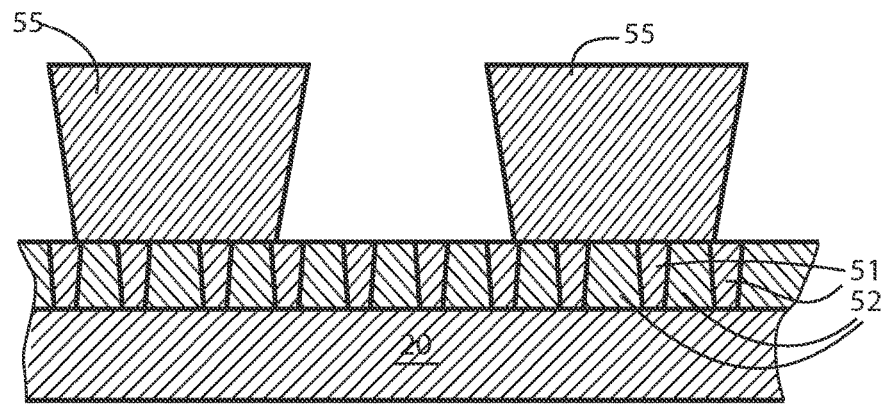
Figure 13B:
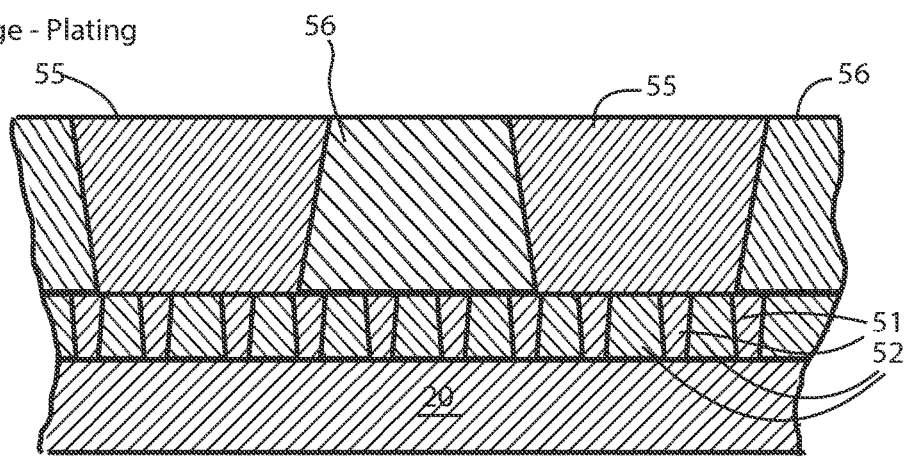
Figure 14:
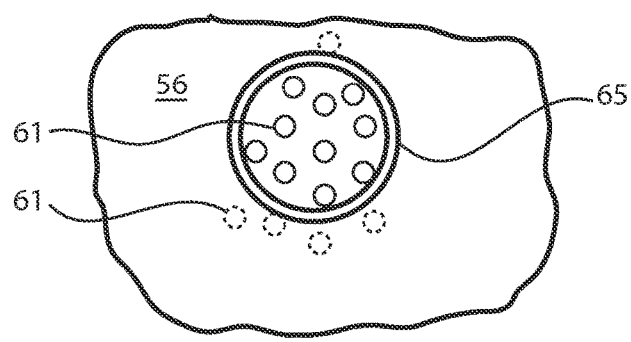

FIGS. 11(a), 11(b) and 12 are views equivalent to FIGS. 4(a), 4(b), and 5 for a second embodiment, in which the holes are tapered; and FIGS. 13(a) and 13(b) are views equivalent to FIGS. 6(a) and 6(b), and for the second embodiment, and FIG. 14 is a plan view in the region of one large upper hole after removal of the photo-resist mask.

Referring to FIG. 4(a) a mandrel 20 has a photo-resist 21 applied in a pattern of vertical columns having the dimensions of holes or pores of the aperture plate to be produced. The column height is preferably in the range of 5 μm to 40 μm height, and more preferably 5 μm to 30 μm, and most preferably 15 μm to 25 μm. The diameter is preferably in the range of 1 μm to 10 μm, and most preferably about 2 μm to 6 μm diameter. This mask pattern provides the apertures which define the aerosol particle size. They are much greater in number per unit of area when compared to the prior art; a twenty-fold increase is possible, thus having up to 1000 holes per square mm.

Referring to FIGS. 4(*b*) and 5 there is electro-deposition of metal 22 into the spaces around the columns 21.

As shown in FIG. 6(*a*) there is further application of a second photo-resist mask 25, of much larger (wider and taller) columns, encompassing the area of a number of first columns 21. The hole diameter in the second plating layer are between 20 μm and 400 μm and more preferably between 40 μm and 150 μm. To ensure higher flow rates this diameter is produced at the upper end of the range and to assure lower flow rates it is produced at the lower end of the range to close more of the smaller openings on the first layer.

Referring to FIGS. 6(*b*) and 7 the spaces around the photo-resist 25 are plated to provide a wafer body 26 on the mandrel 20. When the photo-resist 21 and 25 is cleaned with resist remover and rinsed away the plated material 22 and 26 is in the form of an aperture plate blank or mask 30, as shown in FIG. 8, having large top apertures 32 and small bottom apertures 33.

As shown in FIG. 9 the wafer 30 is punched into a dome shape to provide a final product aperture plate 40.

In more detail, the mandrel 20 is coated with the photo resist 21 with a column height and width equal to the target hole dimension. This coating and subsequent ultraviolet (UV) development is such that columns 21 of photo-resist are left standing on the mandrel 20. These columns are of the required diameter and are as high as their rigidity will support. As the columns are only less than 10 μm, and preferably less than 6 μm in diameter it is possible to get many more columns and resulting holes per unit of area than in the prior art. It is expected that there may be as many as twenty times more holes than in the prior art. This creates potential for a substantial increase in the proportion of open area and resultant nebulizer output.

The mandrel 20 with the selectively developed photo resist in the form of upstanding columns 21 is then placed in the plating bath and through the process of electro-deposition containing the metals Palladium Nickel (PdNi) in liquid form typically is then imparted to the surface. The plating activity is stopped when the height of the columns is reached. No over-plating is allowed as the plating is stopped just as it reaches the height of the columns of photo resist. The plating solution is chosen to suit the desired aperture plate dimensions and operating parameters such as vibration frequency. The Pd proportion may be in the range of about 85% to 93% w/w, and in one embodiment is about 89% w/w, the balance being substantially all Ni. The plated structure preferably has a fine randomly equiaxed grain microstructure, with a grain size from 0.2 μm to 2.0 μm for example. Those skilled in the electrodeposition field art will appreciate how plating conditions for both plating stages may be chosen to suit the circumstances, and the entire contents of the following documents are herein incorporated by reference: U.S. Pat. Nos. 4,628,165, 6,235,117, U.S. 2007023547, U.S. 2001013554, WO2009/042187, and Lu S. Y., Li J. F., Zhou Y. H., "Grain refinement in the solidification of undercooled Ni-Pd alloys", Journal of Crystal Growth 309 (2007) 103-111, Sept 14 2007. Generally, most electroplating solutions involving Palladium and Nickel would work or Nickel only or indeed Phosphorous & Nickel (14:86) or Platinum. It is possible that a non-Palladium wafer could be plated at the surface (1-3 microns thick) in PdNi to impart more corrosion resistance. This would also reduce the hole sizes if smaller openings were desired.

When removed from the plating bath, the wafer thickness is typically 5-40 μm depending on the height of the columns. Peeling off the wafer at this point would yield a very thin wafer in comparison to the standard 60 μm thickness of the prior art. A wafer of this thickness would lack rigidity, be very difficult to process, and would require complex and expensive changes to the mechanical fabrication of the nebulizer core to achieve a natural frequency equivalent to the state of the art such that the existing electronic control drivers would be useable, which in some cases are integrated into ventilators. Use of a different drive controller would be a significant economic barrier to market acceptance due to the costs involved.

This problem is overcome by offering the plated mandrel to the second photo resist deposition process. In one embodiment, the photo resist thickness is placed to a depth equal to that required to bring the overall wafer thickness to approximately 60 µm (similar to the prior art wafer thickness). The second mask height is preferably in the range of 40-50 µm for many applications. It is then developed to allow larger columns to stand on the plated surface. These are typically of a diameter between 40-100 µm but could be larger or smaller. The additional height from the second plating aids removal from the mandrel, but importantly it also achieves a particular thickness which is equivalent to the prior art aperture plate thickness to allow the end product aperture plate 40 to be electrically driven by the existing controllers on the market. This creates a natural frequency matching to achieve correct vibration to generate an aerosol. In general, the second plating stage provides a thickness more suited to the nebulizer application for rigidity, flexibility and flexural strength. Another aspect is that it occludes some of the smaller holes, thereby achieving improved control over flow rate. Hence, the second masking and plating stage can be used to "tune" the end product aperture plate according to desired flow rate. Also, it may be rapidly changed between small batches to enable a wide range of differently tuned plates.

The wafer is then carefully peeled from the substrate without the aid of any subsequent processes such as etching or laser cutting. This ease of peeling has the advantages of not imparting additional mechanical stresses into an already brittle wafer. The wafer is then washed and rinsed in photo-resist remover prior to metrology inspection.

In the aperture plate blank or mask 30 the holes 33 have a depth equal to the first plating layer and the final wafer thickness will be equal to the sum of both plating layers, see FIGS. 8 and 9. It is then ready for annealing, punching and doming to form the vibrating plate 40 shown in FIG. 9.

Advantageous aspects of the invention include:
(i) Greater number of holes per unit of area are possible
(ii) Smaller and more diametrically accurate hole sizes are possible.
(iii) Similar thickness to existing commercially available wafers, which alleviates the onerous need to re-design the nebulizer to match the correct frequency for the existing controllers to activate the aerosol generator.
(iv) Only two plating layers or plating steps are required
(v) Still easy to carefully peel the wafer from the mandrel substrate.
(vi) Possible to use existing electronic controllers to drive the aperture plate as the natural frequencies are matched, having achieved similar aperture plate thickness.
(vii) Possible to get smaller and more controllable particle sizes (2-4 µm).
(viii) Possible to achieve higher flow rates (0.75-1.5 ml/min)
(ix) Possible to achieve flow rates and particle size more independent of each other when compared to the prior art as described. (Typically in the prior art, the increasing flow rate usually requires increasing particle size and vice versa). These advantages are illustrated in the plot of FIG. 10.

Referring to FIGS. 11 to 14 in a second embodiment the processing is much the same as for the above embodiment. In this case however, both of the sets of photo-resist columns are tapered so that the resultant holes are tapered for improved flow of aerosol liquid. There is a mandrel 50, first mask columns 51 and in-between plating 52. The second mask comprises tapered columns 55, and the spaces in-between are plated with metal 56. Greater care is required for the plating steps to ensure that there is adequate plating under the mask overhangs. FIG. 14 shows a plan view, in this case after removal of the photo resist. It will be seen that there are several small holes 61 for each large top hole 65 in the PdNi body 56/52. The top hole 65 has the effect of a funnel down to the small holes 61, which themselves are funnel-shaped.

The invention is not limited to the embodiments described but may be varied in construction and detail. For example, it is envisaged that the second cycle of masking and plating may not be required if the wafer can be removed from the mandrel, either due to the required wafer depth being achieved in the first stage or due to improved wafer-removal technologies being available. In addition, a third layer could be applied to provide more mechanical rigidity to the aperture plate. Also, in the embodiments described above the layers are of the same metal. However it is envisaged that they may be different, and indeed the metal within each hole-forming layer may include sub-layers of different metals. For example the composition at one or both surfaces may be different for greater corrosion resistance and/or certain hydrophilic or hydrophobic properties. Also, there may be an additional plating step for the top 1 to 5 µm or 1 to 3 µm surface layer.

The invention claimed is:

1. A method of manufacturing an aperture plate wafer of an aerosol-forming device, the method comprising:
   providing a mandrel of conductive material,
   applying a first mask over the mandrel in a pattern of first columns,
   electroplating around said first columns to provide first electroplated material,
   removing the first mask to provide said first electroplated material with aerosol-forming holes where the first columns were,
   applying a second mask directly onto said first electroplated material and first columns or aerosol-forming holes, said second mask having second columns which are wider and taller than said first columns and which overlie the area of a plurality of first columns or a plurality of said aerosol-forming holes,
   electroplating around said second columns to provide second electroplated material,
   removing said second mask to provide spaces where said second columns were, each said space directly overlying a plurality of said aerosol-forming holes, and in which
   said second electroplated material completely occludes some of said aerosol-forming holes,
   removing said first and second electroplated material from said mandrel so as to form said aperture plate wafer, and
   said aperture plate wafer is a two-layer structure comprising only said first and second electroplated material.

2. The method as claimed in claim 1, wherein the first columns have a height in the range of 5 µm to 40 µm.

3. The method as claimed in claim 1, wherein the first columns have a width dimension in the plane of the mandrel in the range of 1 µm to 10 µm.

4. The method as claimed in claim 1, wherein the second electroplating brings the aperture plate wafer thickness to a value in the range of 45 μm to 90 μm.

5. The method as claimed in claim 1, wherein applying the first mask and electroplating around said first columns to provide said first electroplated material are performed so that the aerosol-forming holes are tapered in a funnel-shape.

6. The method as claimed in claim 1, wherein applying the second mask and electroplating around said second columns to provide said second electroplated material are performed so that the spaces are tapered in a funnel-shape.

7. The method as claimed in claim 1, wherein at least one of the first electroplated material and the second electroplated material includes Ni.

8. The method as claimed in claim 1, wherein at least one of the first electroplated material and the second electroplated material includes Pd.

9. The method as claimed in claim 1, wherein both Ni and Pd are present in at least one of the first electroplated material and the second electroplated material.

10. The method as claimed in claim 1, wherein both Ni and Pd are present in at least one of the first electroplated material and the second electroplated material; and
 wherein the proportion of Pd is greater than the proportion of Ni.

11. The method as claimed in claim 1, further comprising processing the aperture plate wafer to provide an aperture plate configured to fit into the aerosol-forming device.

12. The method as claimed in claim 1, further comprising processing the aperture plate wafer to provide an aperture plate configured to fit into the aerosol-forming device; and
 wherein the aperture plate wafer is punched into a non-planar shaped aperture plate.

13. The method as claimed in claim 1, further comprising processing the aperture plate wafer to provide an aperture plate configured to fit into the aerosol-forming device; and
 wherein the aperture plate wafer is punched into a shape having an operative dome-shaped part and a flange for engaging a drive.

14. The method as claimed in claim 1, further comprising processing the aperture plate wafer to provide an aperture plate configured to fit into the aerosol-forming device;
 wherein the aperture plate wafer is punched into a non-planar shaped aperture plate; and
 wherein the aperture plate wafer is annealed before punching.

15. The method as claimed in claim 1, wherein applying the second mask and electroplating around said second columns to provide said second electroplated material brings the aperture plate wafer thickness to a value above 50 μm.

16. The method as claimed in claim 1, wherein applying the second mask and electroplating around said second columns to provide said second electroplated material brings the aperture plate wafer thickness to a value greater than 58 μm.

17. A method of manufacturing an aperture plate wafer of an aerosol-forming device, the method comprising:
 providing a mandrel of conductive material,
 applying a first mask over the mandrel in a pattern of first columns,
 electroplating around said first columns to provide first electroplated material,
 applying a second mask directly on said first electroplated material and first columns, said second mask having a plurality of second columns, each of said plurality of second columns being taller than the first columns and overlying a plurality of said first columns;
 electroplating around said second columns to provide second electroplated material,
 removing said first and second masks to provide aerosol-forming holes where the first columns were and spaces where said second columns were,
 and said aperture plate wafer comprises at least said first and second electroplated material, and said aperture plate wafer including a first outer surface and a second outer surface, wherein the spaces extend through the first outer surface and the aerosol-forming holes extend through the second outer surface, and
 wherein at least some of said aerosol-forming holes include an opening opposite the second outer surface and which is entirely occluded by the second electroplated material.

18. The method as claimed in claim 17, wherein the first columns have a height in the range of 5 μm to 40 μm, and wherein the first columns have a width dimension in the plane of the mandrel in the range of 1 μm to 10 μm.

19. The method as claimed in claim 17, wherein both Ni and Pd are present in at least one of the first electroplated material and the second electroplated material; and
 wherein the proportion of Pd is greater than the proportion of Ni.

20. The method as claimed in claim 17, further comprising processing the aperture plate wafer to provide an aperture plate configured to fit into the aerosol-forming device.

21. A method of manufacturing an aperture plate wafer of an aerosol-forming device, the method comprising:
 providing a mandrel of conductive material,
 applying a first mask over the mandrel in a pattern of first columns,
 electroplating around said first columns to provide first electroplated material,
 applying a second mask directly on said first electroplated material and first columns, said second mask having a plurality of second columns, at least one of said second columns having a width of at least twice a width of one of the first columns and being taller than a height of one of first columns;
 electroplating around said second columns to provide second electroplated material,
 removing said first and second masks to provide aerosol-forming holes where the first columns were and spaces where said second columns were, and said aperture plate wafer comprises at least said first and second electroplated material;
 wherein at least some of the aerosol-forming holes have a first opening directly and entirely occluded by the second electroplated material and a second opening extending through an exterior surface of the aperture plate wafer.

22. The method as claimed in claim 21, wherein the first columns have a height in the range of 5 μm to 40 μm, wherein the first columns have a width dimension in the plane of the mandrel in the range of 1 μm to 10 μm, and wherein the second columns have a height in the range of 40 μm to 50 μm.

23. The method as claimed in claim 21, wherein both Ni and Pd are present in at least one of the first electroplated material and the second electroplated material; and
 wherein the proportion of Pd is greater than the proportion of Ni.

24. The method as claimed in claim 21, further comprising punching the aperture plate wafer into a shape having an operative dome-shaped part and a flange for engaging a drive.

* * * * *